United States Patent
Al-Khatib

(10) Patent No.: US 9,504,454 B2
(45) Date of Patent: Nov. 29, 2016

(54) TRANSORAL REPAIR OF CHOANAL ATRESIA

(71) Applicant: KING ABDULAZIZ UNIVERSITY, Jeddah (SA)

(72) Inventor: Talal Ahmed Al-Khatib, Jeddah (SA)

(73) Assignee: KING ABDULAZIZ UNIVERSITY, Jeddah (SA)

(*) Notice: Subject to any disclaimer, the term of this patent is extended or adjusted under 35 U.S.C. 154(b) by 52 days.

(21) Appl. No.: 14/084,086

(22) Filed: Nov. 19, 2013

(65) Prior Publication Data

US 2015/0141997 A1 May 21, 2015

(51) Int. Cl.
| A61B 17/00 | (2006.01) |
| A61B 17/16 | (2006.01) |
| A61B 17/56 | (2006.01) |
| A61B 17/24 | (2006.01) |
| A61B 17/28 | (2006.01) |
| A61B 17/29 | (2006.01) |

(52) U.S. Cl.
CPC .......... *A61B 17/00* (2013.01); *A61B 17/1662* (2013.01); *A61B 17/1688* (2013.01); *A61B 17/24* (2013.01); *A61B 17/56* (2013.01); *A61B 17/1631* (2013.01); *A61B 17/1642* (2013.01); *A61B 17/2812* (2013.01); *A61B 2017/2904* (2013.01); *A61B 2217/005* (2013.01); *A61B 2217/007* (2013.01)

(58) Field of Classification Search
CPC .......... A61B 17/1631; A61B 17/1642; A61B 17/1662; A61B 17/1688; A61B 17/00; A61B 17/56
See application file for complete search history.

(56) References Cited

U.S. PATENT DOCUMENTS

| 1,630,239 | A | * | 5/1927 | Binkley et al. | 606/180 |
| 1,636,636 | A | * | 7/1927 | Humble | 606/180 |
| 6,238,400 | B1 | * | 5/2001 | Bays | 606/96 |
| 6,606,995 | B1 | | 8/2003 | Sadek et al. | |
| 8,172,828 | B2 | * | 5/2012 | Chang et al. | 604/509 |
| 8,715,169 | B2 | * | 5/2014 | Chang et al. | 600/116 |
| 8,974,486 | B2 | * | 3/2015 | Kotler | 606/199 |
| 2003/0153937 | A1 | | 8/2003 | Al-Qahtani et al. | |
| 2004/0098006 | A1 | * | 5/2004 | Nakanishi | 606/170 |
| 2004/0127927 | A1 | * | 7/2004 | Adams | 606/170 |

(Continued)

FOREIGN PATENT DOCUMENTS

RU 2157664 10/2000

OTHER PUBLICATIONS

Fitzgerald et al., The transnasal flexible laryngoesophagoscope as an adjunct during surgical correction of choanal atresia, 2012, JLO, 126, 1179-1181.*

(Continued)

*Primary Examiner* — Larry E Waggle, Jr.
(74) *Attorney, Agent, or Firm* — Richard C. Litman

(57) ABSTRACT

The transoral repair of choanal atresia is a method for the surgical repair of choanal atresia that uses a transoral approach. The procedure includes the use of a curved drill, a curved shaver, curved grasping forceps, and a suction irrigator. After endotracheal intubation, a retractor is inserted to retract the tongue. A 120° angled telescope is inserted behind the soft palate into the nasopharynx to visualize the posterior choanae. A curved drill is used to drill the atretic plate from the vomer medially to the lateral pterygoid plate laterally. The drilled section of the atretic plate is removed to clear the obstruction.

8 Claims, 4 Drawing Sheets

(56) References Cited

U.S. PATENT DOCUMENTS

| | | | |
|---|---|---|---|
| 2004/0225308 A1* | 11/2004 | Adams | 606/167 |
| 2006/0063973 A1* | 3/2006 | Makower et al. | 600/114 |
| 2006/0095066 A1* | 5/2006 | Chang et al. | 606/199 |
| 2007/0073269 A1* | 3/2007 | Becker | 604/509 |
| 2008/0082045 A1* | 4/2008 | Goldfarb et al. | 604/96.01 |
| 2008/0208265 A1* | 8/2008 | Frazier et al. | 606/326 |
| 2010/0030113 A1* | 2/2010 | Morriss et al. | 600/585 |
| 2011/0288477 A1* | 11/2011 | Ressemann et al. | 604/95.04 |
| 2014/0066901 A1* | 3/2014 | Dinger et al. | 604/514 |

OTHER PUBLICATIONS

Ha et al., Congenital choanal atresia and pyriform aperture stenosis, 2011, Int'l. Journal of Pediatric Otorhinolaryngology Extra, 6, 265-268.*

Hopf et al., Endoscopic Laser Surgery of Choanal Atresia—The New Retropalatine Approach, 2002, Med. Laser Appl., 17, 243-261.*

McLeod et al., Revision choanal atresia repair, 2003, Int'l. Journal of Pediatric Otorhinolaryngology, 67, 517-524.*

Hassan, M. et al., "Combined Transoral-Transnasal Approach in the Repair of Congenital Posterior Choanal Atresia: Clinical Experience", J. Otolaryngol. Head Neck Surg., 2011, 40(3), 271-276.

Tiessier, Natacha et al., "Predictive Factors for Success After Transnasal Endoscopic Treatment of Choanal Atresia", Arch. Otolaryngol. Head Neck Surg., 2008, 134(1), 57-61.

Wang, Qin Ying et al., "Repair of Acquired Posterior Choanal Stenosis and Atresia by Temperature-controlled Radio Frequency With the Aid of an Endoscope", Arch. Otolaryngol. Head Neck Surg., 2009, 135(5), 462-466.

* cited by examiner

TRANSORAL REPAIR OF CHOANAL ATRESIA

BACKGROUND OF THE INVENTION

1. Field of the Invention

The present invention relates to surgical procedures, and particularly to transoral repair of choanal atresia.

2. Description of the Related Art

Choanal atresia is a congenital obstruction of the back of the nose (posterior choanae) that prevents communication between the nose and nasopharynx. The incidence is around 1 in every 5,000 births. It results from failure of canalization of the posterior choanae. When the atresia is bilateral, it presents a life-threatening situation that has to be dealt with in the early days of life.

Traditionally, repair of choanal atresia was done blindly using puncture dilators through the nose. This technique was first described by Emmert in 1854. Recurrence rates were high and required multiple dilation to achieve patency.

Subsequently, repair was done via the transpalatal approach. This approach involves incising the soft palate to reach the posterior choanae. This approach was successful and showed lower recurrence rates, but unfortunately had more complications. Complications of this approach include wound dehiscence, fistula formation, and interruption of palatal growth. These complications lead to dentition problems and cross-bite deformity in children.

With the advent of endoscopic techniques, surgeons used small endoscopes to reach the posterior choanae transnasally. This transnasal approach became more popular and almost replaced the transpalatal approach. Recurrence of choanal atresia after transnasal approach is more common than the old transpalatal approach, but due to fewer complications, surgeons have stuck with the least invasive technique. Recurrence has been shown to be more common if the endoscopic procedure was done in the neonatal period (first 30 days of life). The reason for recurrence is thought to be due to the young age of neonates, and possibly also due to intrinsic factors that led to the stenosis in the first place playing a role in re-stenosis.

The present inventor believes that recurrence in the neonatal period is due to difficult access and incomplete removal of the atretic plate (stenosis), rather than the young age of children. In addition, neonates have small nasal passages, and the transnasal approach might be difficult, especially if endoscopic shaver or drilling of lateral pterygoid plates is required. Associated nasal abnormalities, such as mid-nasal stenosis, make the transnasal approach even more difficult.

Therefore, transoral repair of choanal atresia solving the aforementioned problems is desired.

SUMMARY OF THE INVENTION

The transoral repair of choanal atresia is a method for the surgical repair of choanal atresia that uses a transoral approach. The procedure includes the use of a curved drill, a curved shaver, curved grasping forceps, and a suction irrigator. After endotracheal intubation, a retractor is inserted to retract the tongue. A 120° angled telescope is inserted behind the soft palate into the nasopharynx to visualize the posterior choanae. A curved drill is used to drill the atretic plate from the vomer medially to the lateral pterygoid plate laterally. The drilled section of the atretic plate is removed to clear the obstruction.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
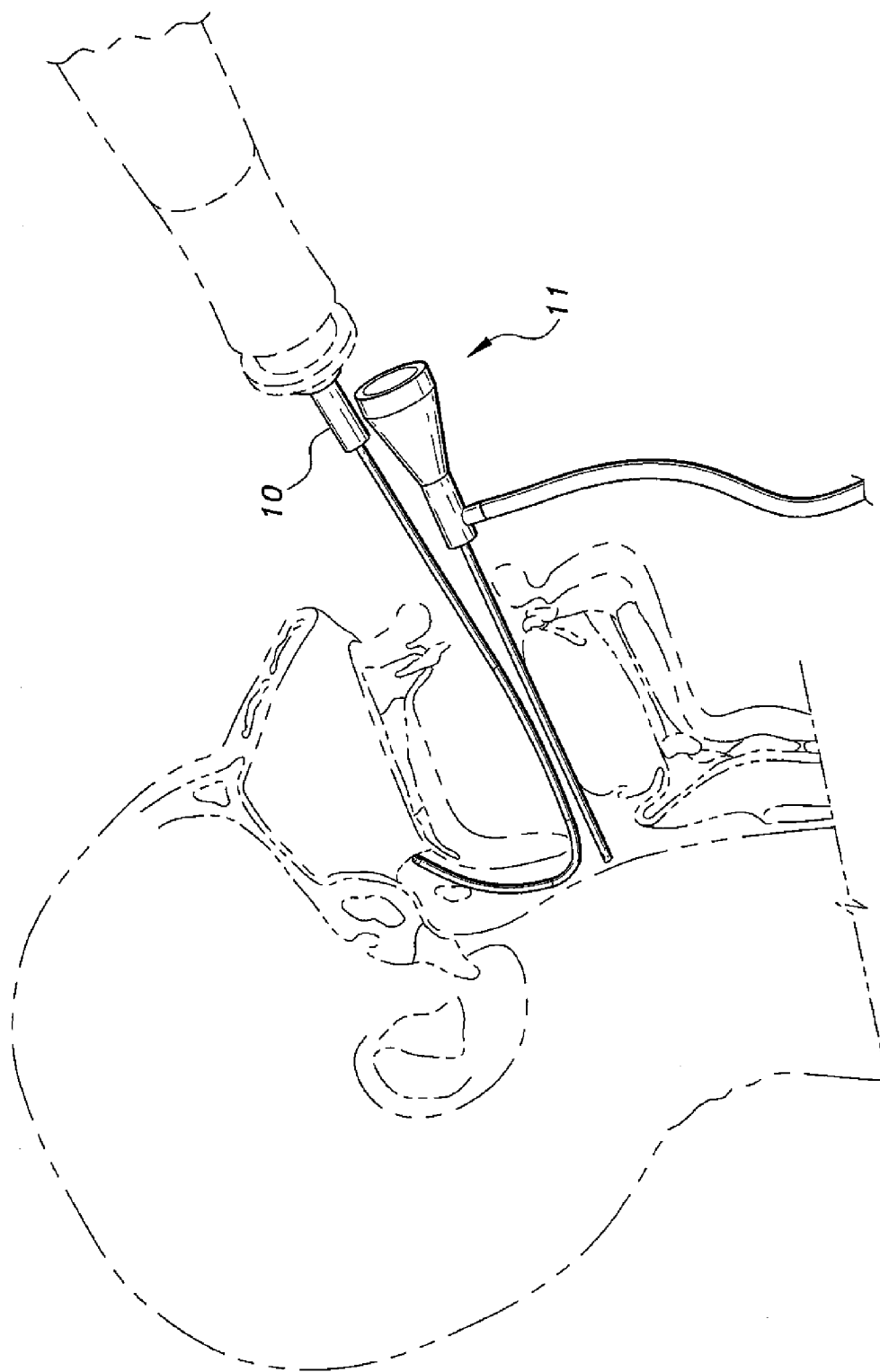
FIG. 1 is a diagrammatic perspective view of the approach in transoral repair of choanal atresia according to the present invention.

Transoral repair of choanal atresia is a method that for clearing an obstruction between the nose and the nasopharynx that results from failure of recanalization of the nasal fossa during fetal development. The procedure begins with endotracheal intubation to maintain a patent airway. Then, after endotracheal intubation, a Dingman mouth gag retractor is inserted to retract the tongue. As shown in FIG. 1, a 120° angled telescope 11 is inserted behind the soft palate into the nasopharynx to visualize the posterior choanae. The following surgical landmarks are identified: (1) the atretic plate; (2) the posterior end of the vomer bone; and (3) the torus tubarius. A curved drill is inserted transorally. Under direct vision, drilling of the atretic plate is carried out from the vomer medially (posterior nasal septum) until the lateral pterygoid plate laterally. Any bone dust is removed and vacuumed, and heat generated by the drill is reduced by using a suction irrigator in conjunction with the curved drill. Any soft tissue component of the atresia is removed using a curved shaver, and any bony spicules or fractured bony part of the atretic plate is removed using a curved grasping forceps. Care is taken not to drill deep into the nasal cavity to avoid injury to the posterior end of the inferior turbinate. This approach might be extremely helpful in case of a thickened vomer bone, where a reduction in size is essential.

The specifications of the instruments used in the transoral repair of choanal atresia are listed below.

The drill is composed of a drill handle, a shaft and a drill bit. The drill shaft needs to be long and curved to reach the nasopharynx from the mouth. The drill bit needs to be rounded with different sizes, including 4 mm, 3 mm and 2 mm, similar to otologic drill bits. The drill bit needs to have a diamond head. The drill 10 is also shown in FIG. 1.

Figure 2:
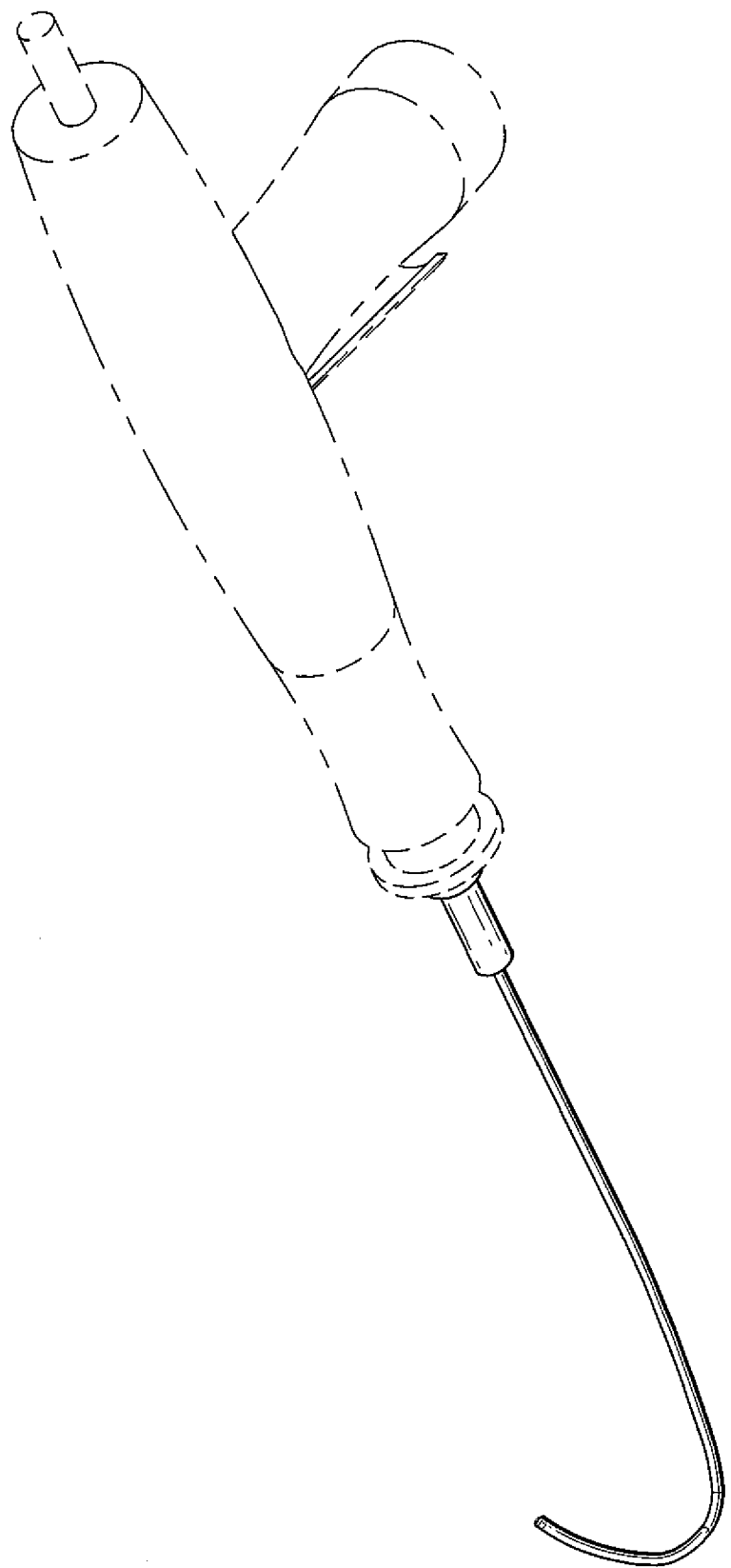
FIG. 2 is a perspective view of a curved shaver used in transoral repair of choanal atresia according to the present invention.

A curved shaver is used for microdebriding redundant soft tissue and excess mucosa. This microdebridment minimizes soft tissue fibrosis and restenosis. The shaver blade needs to rotate 360° to accommodate all borders of choana. The curved shaver is shown in FIG. 2.

Figure 3:
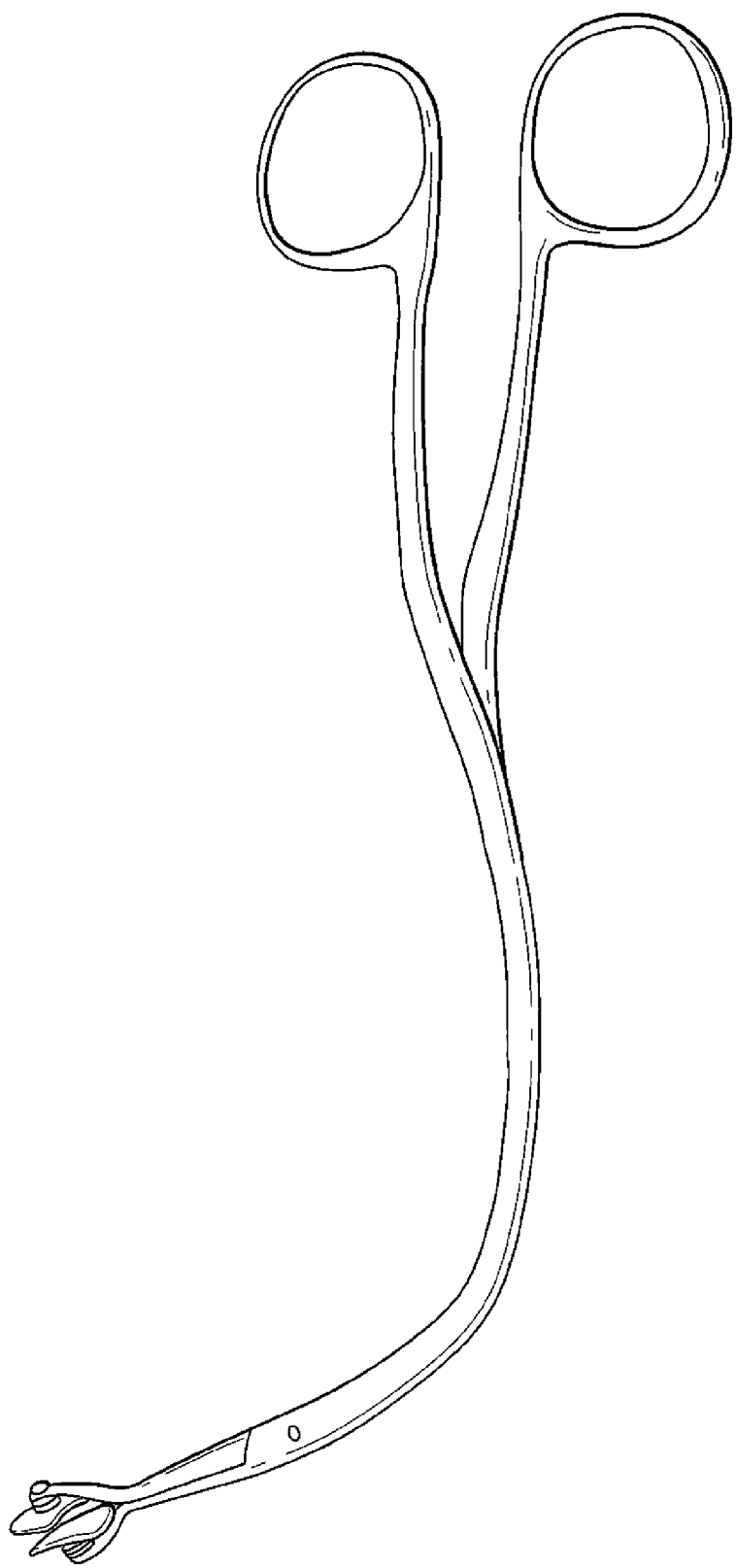
FIG. 3 is a perspective view of a curved grasping forceps used in transoral repair of choanal atresia according to the present invention.

A crocodile or curved grasping forceps is used to grasp bone spicules and remove them. This instrument is complementary to the drill. Certain areas, e.g., the choana, require delicate removal of bone using forceps, rather than using the high speed drill. In addition, at the completion of drilling, final touches and removal of excess mucosa can be done by this forceps. The curved grasping forceps is shown in FIG. 3.

Figure 4:
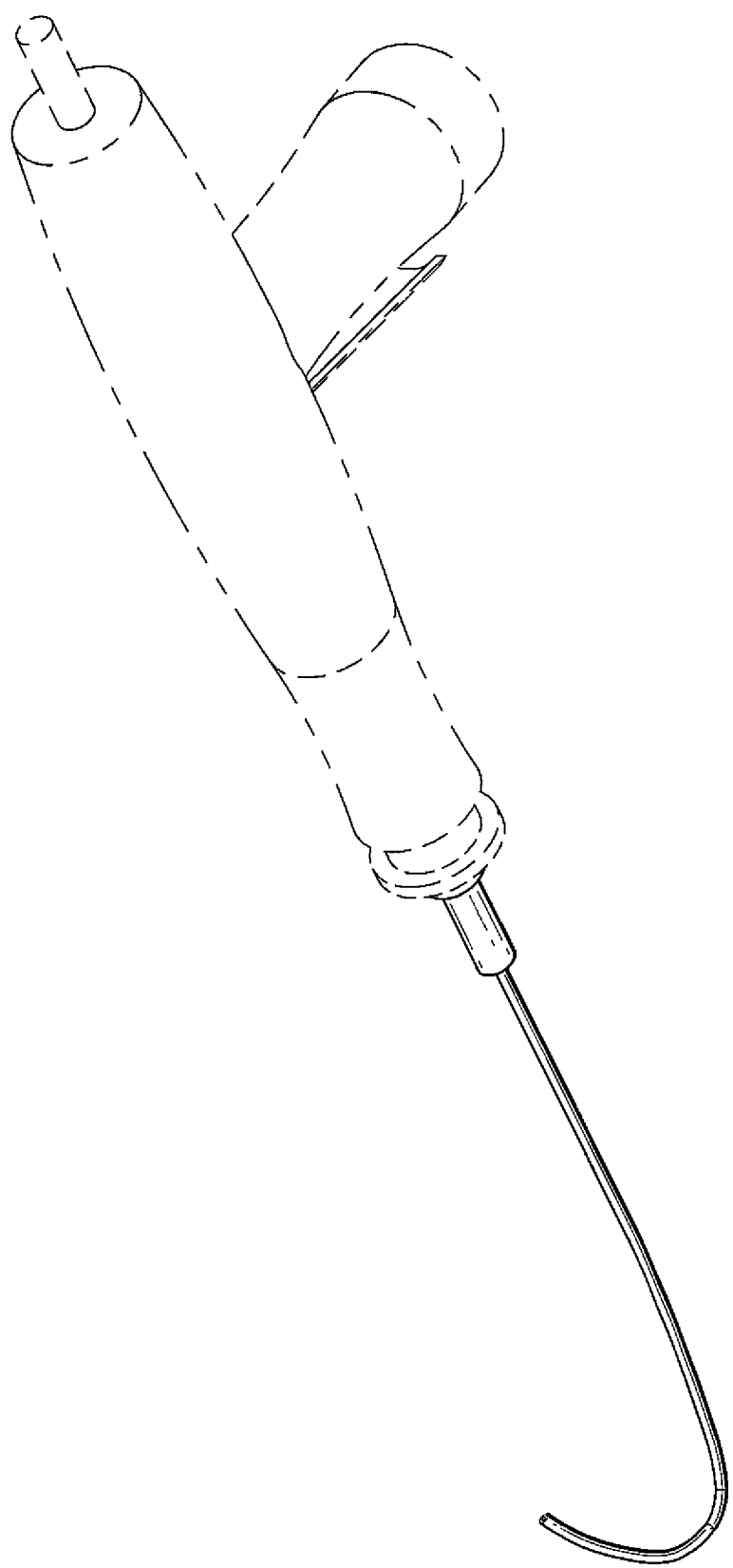
FIG. 4 is a perspective view of a curved suction irrigator used in transoral repair of choanal atresia according to the present invention.

A suction irrigator is used for choanal atresia repair. Water irrigation is used while drilling to wash out bone dust and suction the smoke. The operative field needs to be cleaned frequently to provide optimum visualization to carry out the repair. An example of the suction irrigator is shown in FIG. 4.

Transoral repair of choanal atresia provides direct access to the area of narrowing, better and wider space to work with in young children (instead of working through narrow nasal passages), reduces intranasal trauma and subsequent narrowing, allows better resection of pathology (atretic plate and widened vomer), and reduces the need for multiple revision surgeries.

It is to be understood that the present invention is not limited to the embodiments described above, but encompasses any and all embodiments within the scope of the following claims.

I claim:

1. A method for transoral repair of choanal atresia in a human patient, comprising the steps of:
    (a) intubating a trachea of the human patient;
    (b) inserting a mouth gag retractor to retract a tongue of the human patient;
    (c) inserting a 120° telescope behind a soft palate of the human patient into a nasopharynx of the human patient to visualize posterior choanae of the human patient;
    (d) identifying the following surgical landmarks in the human patient:
        (1) an atretic plate;
        (2) a posterior end of a vomer bone and
        (3) a torus tubarius;
    (e) inserting a curved drill transorally into the nasopharynx;
    (f) drilling the atretic plate from the vomer bone medially at a posterior nasal septum of the human patient until a lateral pterygoid plate of the human patient laterally;
    (g) removing and vacuuming any bone dust and reducing heat generated by the drill using a suction irrigator in conjunction with the curved drill;
    (h) removing any soft tissue component of the atresia using a curved shaver; and
    (i) removing any bony spicules or fractured bony parts of the atretic plate using a curved grasping forceps.

2. The method for transoral repair of choanal atresia according to claim 1, wherein the drill comprises a drill handle, a curved shaft and a drill bit.

3. The method for transoral repair of choanal atresia according to claim 2, wherein said drill bit is rounded.

4. The method for transoral repair of choanal atresia according to claim 2, wherein a size of said drill bit is selected from the group consisting of 2 mm, 3 mm and 4 mm.

5. The method for transoral repair of choanal atresia according to claim 1, wherein said shaver is rotatable by 360°.

6. The method for transoral repair of choanal atresia according to claim 1, wherein the curved grasping forceps is a crocodile forceps.

7. The method for transoral repair of choanal atresia according to claim 1, wherein said suction irrigator is curved.

8. The method for transoral repair of choanal atresia according to claim 1, wherein said suction irrigator is straight.

* * * * *